(12) United States Patent
Gibbs et al.

(10) Patent No.: US 9,326,836 B2
(45) Date of Patent: May 3, 2016

(54) SINGLE USE PERIODONTAL PROBE

(75) Inventors: Charles H. Gibbs, Gainesville, FL (US); Chris Gibbs, Gainesville, FL (US)

(73) Assignee: FLORIDA PROBE CORPORATION, Gainesville, FL (US)

( * ) Notice: Subject to any disclaimer, the term of this patent is extended or adjusted under 35 U.S.C. 154(b) by 959 days.

(21) Appl. No.: 12/475,783

(22) Filed: Jun. 1, 2009

(65) Prior Publication Data

US 2009/0298005 A1    Dec. 3, 2009

Related U.S. Application Data

(60) Provisional application No. 61/057,823, filed on May 31, 2008.

(51) Int. Cl.
*A61C 19/04*    (2006.01)

(52) U.S. Cl.
CPC ..................... *A61C 19/043* (2013.01)

(58) Field of Classification Search
CPC ................. A61C 19/04; A61C 43/041; A61B 2019/462; Y10T 408/21
USPC ............ 433/29, 72, 75, 141, 80–90; 128/776, 128/777; 33/513–514; 604/110, 117
See application file for complete search history.

(56) References Cited

U.S. PATENT DOCUMENTS

| | | | |
|---|---|---|---|
| 3,943,914 A * | 3/1976 | Grenfell et al. | 600/589 |
| 4,203,223 A | 5/1980 | Lautenschlager et al. | |
| 4,250,895 A * | 2/1981 | Lees | 600/589 |
| 4,340,069 A | 7/1982 | Yeaple | |
| 4,665,621 A | 5/1987 | Ackerman et al. | |
| 4,791,940 A * | 12/1988 | Hirschfeld et al. | 600/589 |
| 4,968,252 A * | 11/1990 | Creps | 433/229 |
| 5,137,447 A * | 8/1992 | Hunter | 433/72 |
| 5,197,487 A * | 3/1993 | Ackerman et al. | 600/589 |
| 5,419,703 A * | 5/1995 | Warrin et al. | 433/216 |
| 5,486,109 A * | 1/1996 | Hunter et al. | 433/72 |
| 5,919,129 A * | 7/1999 | Vandre | 600/170 |
| 5,993,209 A | 11/1999 | Matoba et al. | |
| 6,162,202 A * | 12/2000 | Sicurelli et al. | 604/272 |
| 2003/0143510 A1 * | 7/2003 | Berube-Lauziere et al. | 433/29 |
| 2004/0248058 A1 * | 12/2004 | Hahn et al. | 433/29 |
| 2006/0154199 A1 * | 7/2006 | Maxwell et al. | 433/72 |

FOREIGN PATENT DOCUMENTS

WO    WO 9011046 A1 * 10/1990    ............... A61B 5/10

\* cited by examiner

*Primary Examiner* — Matthew Nelson
(74) *Attorney, Agent, or Firm* — Saliwanchik, Lloyd & Eisenschenk

(57) ABSTRACT

The subject invention provides single use periodontal probes. In preferred embodiments as described herein the probes of the subject invention can be used with a recording apparatus for simultaneously measuring and recording the depth of the periodontal pocket (gingival sulcus) and more particularly, to a unit employing a periodontal depth probe operably connected to a recording device, capable of producing a permanent visual record of the measured pocket depth. In further embodiments, the probes of the subject invention can be used to deliver and/or collect materials for prevention, treatment and/or diagnosis of periodontal conditions.

16 Claims, 14 Drawing Sheets

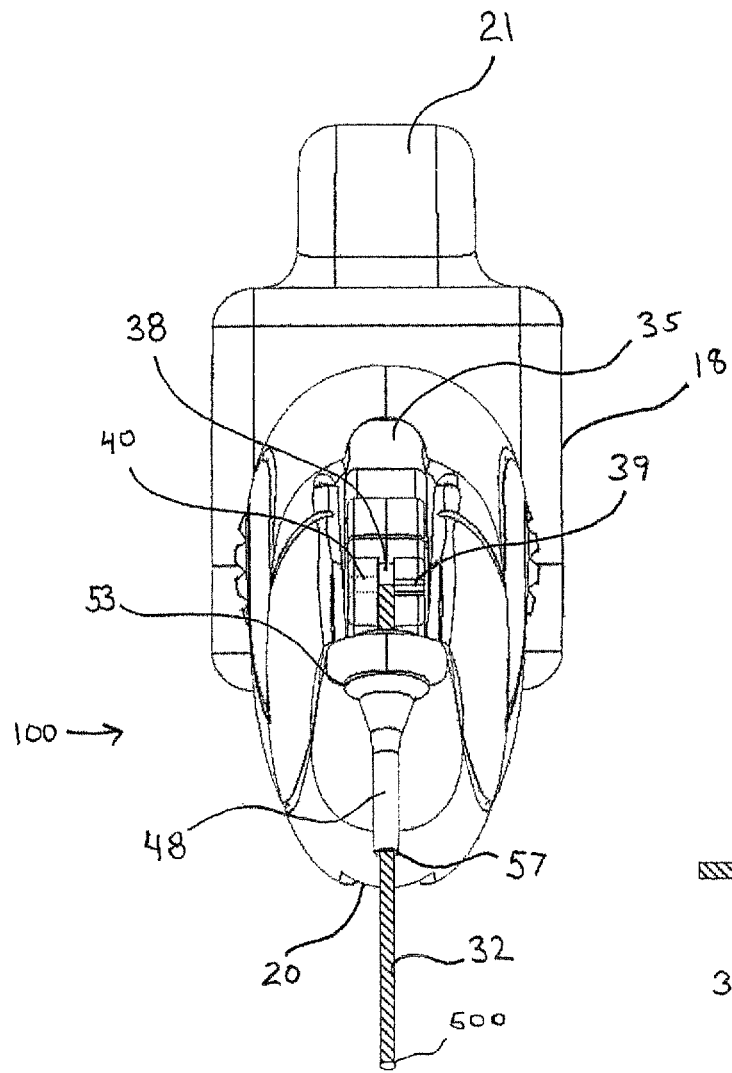
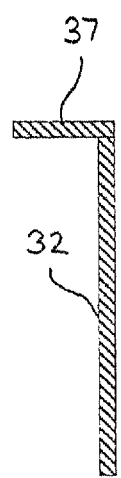
FIG. 4A
FIG. 4B

SINGLE USE PERIODONTAL PROBE

CROSS-REFERENCE TO A RELATED APPLICATION

This application claims the benefit of U.S. provisional application Ser. No. 61/057,823, filed May 31, 2008, which is incorporated herein by reference in its entirety.

BACKGROUND OF INVENTION

Periodontal disease is commonly known as pyorrhea and is the result of bacteria spreading below the gum line, causing teeth and gums to separate forming spaces or pockets. As the disease progress, the pockets become larger and are filled with bacteria and pus, and in time, destruction of the tissue attachment to the teeth and destruction of the supporting bone structure occurs.

In the United States, periodontal disease is the leading cause of tooth loss in adults over 30 years of age. Periodontal disease is usually painless, site specific and goes through periods of exacerbation and remission, making accurate detection and monitoring imperative in the field of dentistry.

Measurement of pocket depth is a primary method for detecting periodontal (gum) disease. It is common knowledge that early detection and periodic measurements at several locations, as many as six per tooth, is necessary to determine if the gingival sulcus (pocket) is enlarging and how fast. There are many instruments used to measure and record the depth of the pocket, such as, for example, the Ward discloses, in U.S. Pat. No. 3,058,225, a periodontal probe having a handle with a protruding sleeve and flexible probe tip that connects directly to a mechanical indicator or indirectly to an electric current indication device located on the probe handle. There are disadvantages with this type of probe. The sleeve is long and difficult to keep clean. Blood and other body fluids can create deposits inside the sleeve, which can interfere with the smooth movement of the probe tip. These deposits tend to become hardened and more of a problem following procedures of heat sterilization. Therefore, it can be helpful to employ a shorter sleeve that is open and easy to clean. Further, the Ward device does not utilize an automatic recording device, but requires the dentist to make all measurements by taking his eyes off the tip and observing the indicator, resulting in lost time. Since there are as many as six measurements per tooth, and the normal mouth has as many as thirty-two teeth, the time lost in taking as many as 192 separate measurements is considerable.

Grenfell et al., disclose a periodontal probe, in U.S. Pat. No. 3,943,914 that has an electrically connected remote recording console that provides a permanent record of the depth of the gingival sulci around a particular tooth. However, the Grenfell et al. probe has a long, rigid, sleeve, which can be difficult to keep clean.

There are several commercially available periodontal probes. For example, The Vine Valley Research Corp. offers a unit that sounds a "beep" when a preset probing force is reached. This unit, originally developed by Dr. Ronald N. Yeaple and disclosed in U.S. Pat. No. 4,340,069, does not electronically measure pocket depth, only probing pressure.

A published article in The Journal of Periodontology, 1980, Vol. 51, No. 5, pp. 298-300, entitled "A Periodontal Probe that Measures to One Tenth Millimeter", by S. G. Detsch, discusses a probe with a mechanical readout on the handle. It utilizes a caliper attached to a probe tip, where the probe tip slides within a curved sleeve. This probe does have a controlled force and does not provide electronic readout. And, as with other designs, the curved sleeve is long and can be difficult to keep clean.

An article by U. van der Velden and J. K. de Vries that appeared in The Journal of Clinical Periodontology, 1978, Vol. 5, pp. 188-197, entitled "Introduction to a New Periodontal Probe: The Pressure Probe", discusses the use of air pressure to extend a probe tip that slides within a sleeve. During probing, the tip can intrude from the position of maximum extension at a force determined by the present pressure, until the metal sleeve contacts the gum margin. The pocket depth is read from a millimeter scale on the handle. What is not disclosed is that the probe has a remote readout. Further, the use of air pressure to extend the probe requires an additional machine unit. And, as with the other disclosures, the sleeve is long and can be difficult to keep clean.

Other disclosures include U.S. Pat. No. 4,203,223, granted to Lautenschlager et al., which describes a periodontal probe that provides a constant force and a relatively short sleeve, which is advantageous for cleaning. However, pocket depths must be read visually, as with common probes, because there is no means for automatic reading or measurement.

Ackerman et al., in U.S. Pat. No. 4,665,621, described a periodontal probe with frictional means for limiting probing force, electronic measurement, and a microcomputer for analyzing and displaying the data. Disadvantageously, the probe has a long, curved sleeve, which is difficult to clean. The curved portion of the sleeve adds friction during movement. The probe tip is extended into the gingival sulcus by pressing a control sleeve. This can be inconvenient due to the difficulty of simultaneously sliding a sleeve and positioning the probe tip in the gingival sulcus.

Further, Hirschfeld et al., in U.S. Pat. No. 4,791,940, disclose a periodontal probe that maintains a constant probing force by use of a spring, uses a remote readout, and provides electronic measurements for computer recording. Advantageously, the sleeve is relatively short, stationary, and fairly flexible. The probe also includes a locking button for controlling the probe tip, allowing a dentist to lock the tip in order to probe at forces greater than that provided by the spring. While this probe solved some prior disadvantages, it requires sterilization of the probe tip after each procedure, and did not include a lighting mechanism for viewing the back of the mouth. In addition, the locking button on the top of the probe could be more often inadvertently pressed by the dentist during a probing procedure.

Matoba et al., in U.S. Pat. No. 5,993,209, disclosed a probe in which the sleeve is flexible for easier maneuvering of the probe and the elongated sleeve projects from the hand piece to facilitate cleaning and sterilization. The probe is moved through the slider using a sliding operating member that is energized by a compressed coil spring. There is a disadvantage here because the very long curved sleeve requires a long curved probe which must also be flexible in order slide easily through the curvature of the sleeve yet rigid enough to provide steady force in the pocket. Additionally there is no indication that the probe force can be controlled.

It can be seen that many of the prior art methods and devices used by periodontists to diagnose and assess the progression of the disease do not provide a controlled, standardized way of probing the gingival sulcus, and often result in only crude measurements. Furthermore, the necessity of having to clean and sterilize devices between uses is a hindrance to the speed and efficiency at which patients can be treated. There is a need for better devices and methods of making rapid, accurate measurements in a standardized fashion in order to diagnose and measure the progression of periodontal disease.

BRIEF SUMMARY

The subject invention provides single use periodontal probes. In preferred embodiments as described herein the probes of the subject invention can be used with a recording apparatus for simultaneously measuring and recording the depth of the periodontal pocket (gingival sulcus) and more particularly, to a unit employing a periodontal depth probe operably connected to a recording device, capable of producing a permanent visual record of the measured pocket depth. In further embodiments, the probes of the subject invention can be used to deliver and/or collect materials for prevention, treatment and/or diagnosis of periodontal conditions. Advantageously, in certain embodiments, diagnosis and treatment can occur during the same procedure.

In a specific embodiment, the probe has an elongated body with a movable probe tip and an electronic displacement transducer in operable connection with a wireless link, capable of transmitting data to a recording apparatus. Affixed to the probe tip end of the handle is a stationary sleeve through which the probe tip can reciprocate. The probe tip is connected by a movable arm to one end of a rod that traverses through the handle. The opposite end of the rod is in operable connection with a displacement transducer and a spring. The spring is positioned so that it exerts force against the rod, biasing the rod towards the probe tip, which is forced into a fully extended position through the stationary sleeve.

By using a probe with a movable probe tip under a constant force, the force applied to the bottom of the periodontal pocket is consistent, unlike prior art designs. With the present invention, the probing force is pre-determined by the spring force and remains consistent. In use, when the probe tip touches the bottom of the pocket, force is applied to the tip so that the sleeve slides over the shaft of the tip to contact the margin of the gum. As the probe tip is forced into the sleeve, the rod is pushed towards the opposite end of the handle, causing the displacement transducer to be moved. Once the probe tip and sleeve are in the correct position to measure the depth of the periodontal pocket, the measurement can be automatically recorded.

In one embodiment, the probe is removable and can be detached from the electronic displacement transducer for disposal. Thus, in this embodiment, each probe is used for only a single patient, but each disposable probe can be connected to a single displacement transducer and recording apparatus. This allows a new probe to be used for each patient, but the same displacement transducer can be used to measure the periodontal pockets of more than one patient with a minimum of delay between each patient. Use of the recording apparatus provides good consistency of measurement between each patient.

In a further embodiment, the single-use (disposable) probe, once disconnected from the displacement transducer cannot be re-connected because the connector mechanism of the probe is destroyed when it is disconnected from the displacement transducer.

In a further embodiment, the displacement transducer has a wireless connection to a computer, or other recording device. Connected to the recorder control circuit of the computer can be an operator-controlled foot switch, which is depressed by the probe operator each time it is desired to record the pocket depth being measured by the probe. A record is made each time the foot pedal is depressed. Therefore, an accurate measurement can be obtained without the operator having to lose eye contact with the teeth or having to hand-record each measurement or having to employ an assistant to do so.

Thus, the subject invention provides economical, single use probe devices and methods that allow a user to simultaneously and automatically create a permanent visual record of the depth of each periodontal pocket as it is measured. In further embodiments, the probe of the subject invention provides a constant force that reacts against a force applied to the probe, where such forces are transmitted to a displacement transducer operably connected to a recording device.

BRIEF DESCRIPTION OF DRAWINGS

In order that a more precise understanding of the above recited invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which:

FIG. 4A is a front plan view of the embodiment in FIG. 1, showing the details of the probe tip and sleeve.

FIG. 4B is a front plan view of an embodiment of a probe tip that can be utilized with the probe device of the subject invention.

DETAILED DISCLOSURE

Figure 1:
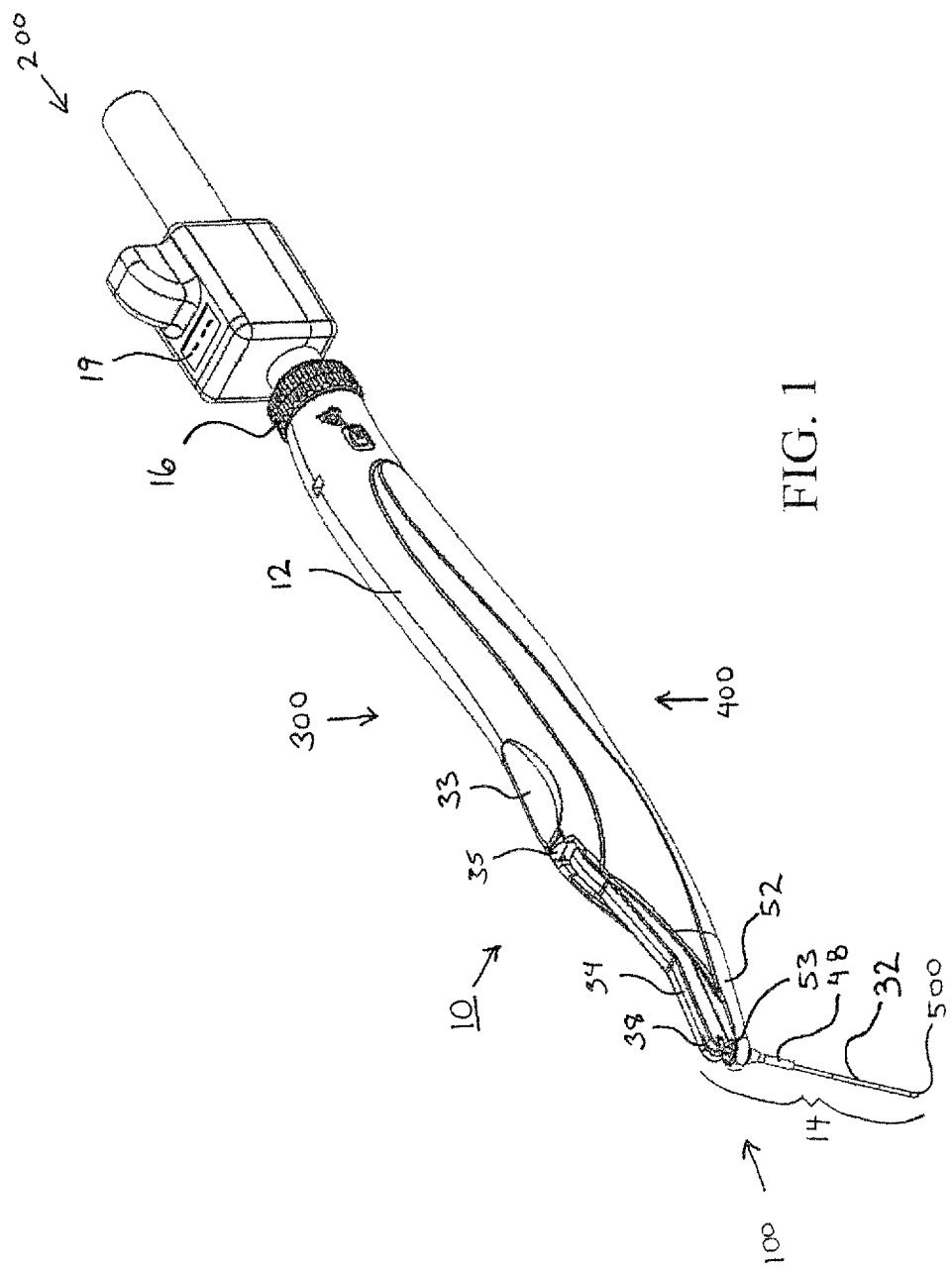
FIG. 1 is an orthographic illustration of an embodiment of the probe device of the subject invention.

The subject invention provides depth-measuring periodontal probes and recording apparatus of the type used by dentists to measure the depth of the pocket between the gum and a tooth. The depth of the pocket, also known as gingival sulcus, is measured from the margin of the gum (the top of the gum) to the epithelial attachment (the point where the gum attaches to the tooth), which forms the bottom of the pocket.

The system of the subject invention provides devices and methods for the diagnosis and/or treatment of periodontal disease. The system includes a single use periodontal probe capable of obtaining consistent measurements, and which eliminates the need for sterilization between uses. The probe can be integrated with a computer so that measurements obtained with the probe can be recorded automatically. In further embodiments, the probe can include mechanisms for the delivery of treatment medicaments at the time of periodontal probing. And in further embodiments, the administration of treatment medicaments can be computer controlled or assisted.

More specifically, the subject invention pertains to one or more embodiment(s) of a single use periodontal probe device capable of recording the depth of a gingival sulcus. Still more specifically, the subject invention pertains to embodiment(s) of a single use periodontal probe measuring device having a probe tip capable of applying a constant force. The probe device of the subject invention obtains and records consistent, accurate measurements during an examination and measurement process. In alternative embodiments, the periodontal device of the subject invention is capable of delivering a medicament to a treatment area.

The periodontal probe and methods of use of the subject invention overcome disadvantages of the prior art. In a preferred embodiment, the probe of the subject invention provides a single use probe with a short, sleeve that eliminates the need for cleaning and/or sterilization. The short sleeve, when manufactured of low weight materials, reduces stress and fatigue on the hand and arm of the user. The single use probe of the subject invention can be operably attached to a housing containing a wireless link to a recorder. The recorder allows measurements to be recorded without interfering with the position and force of the probe. After use, the probe can be disconnected from the housing and disposed of and a new, sterile probe coupled to the housing. In further embodiments, the probe can have a hollow irrigation probe tip that allows application of various medicaments and/or the collection of samples.

The term "patient" as used herein, describes any human or animal to which the devices and methods of the present invention can be applied. Thus, the devices and methods of the subject application can be useful for medical and veterinary purposes.

The terms "clinician", "dentist", "hygienist", "doctor" and "physician" as used in the subject invention are merely for literary convenience. The terms should not be construed as limiting in any way. The devices, apparatuses, methods, techniques and/or procedures of the subject invention could be utilized by any person desiring or needing to do so and having the necessary skill and understanding of the invention.

Also, as used herein, and unless otherwise specifically stated, the terms "operable communication", "operable connection", and "operably connected" mean that the particular elements are connected in such a way that they cooperate to achieve their intended function or functions. The "connection" may be direct, or indirect, physical or remote.

In addition, references to "first", "second", and the like (e.g., first and second end), as used herein, and unless otherwise specifically stated, are intended to identify a particular feature of which there are at least two. However, these references are not intended to confer any order in time, structural orientation, or sidedness (e.g., left or right) with respect to a particular feature.

Referring to the drawings, there is shown in FIGS. 1-6, an instrument embodying a periodontal probe of the present invention. FIG. 1 shows a periodontal probe 10 consisting of a body 12 with an interior cavity 20 and having at the distal end 100 a probe tip 32 and a coupling 16 at the proximal end 200, which connects to a housing 18 containing an electronic displacement transducer 64. In a further embodiment, a digital readout screen 19 within the housing 18, or, optionally, a stand-alone device, is coupled with the electronic displacement transducer permitting a hygienist to see the depth of a pocket by referring to the digital readout.

Figure 3:
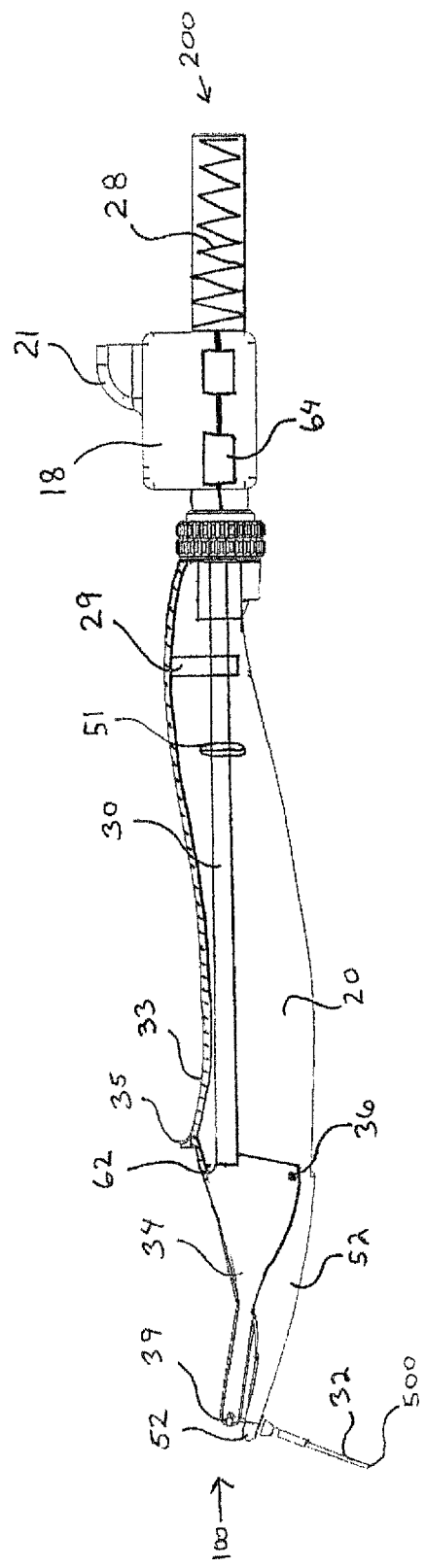
FIG. 3 is a cross-sectional view taken along line A-A' of the embodiment shown in FIG. 2, illustrating the interior of a probe device of the subject invention.
Figure 6:
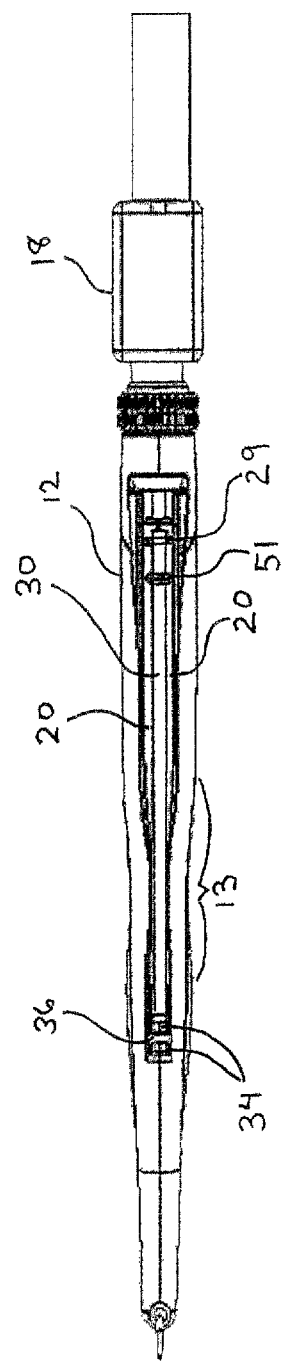
FIG. 6 is a bottom plan view of the embodiment in FIG. 1, showing how the shape of the body aids in positioning of the rod within the handle.
Figure 7:
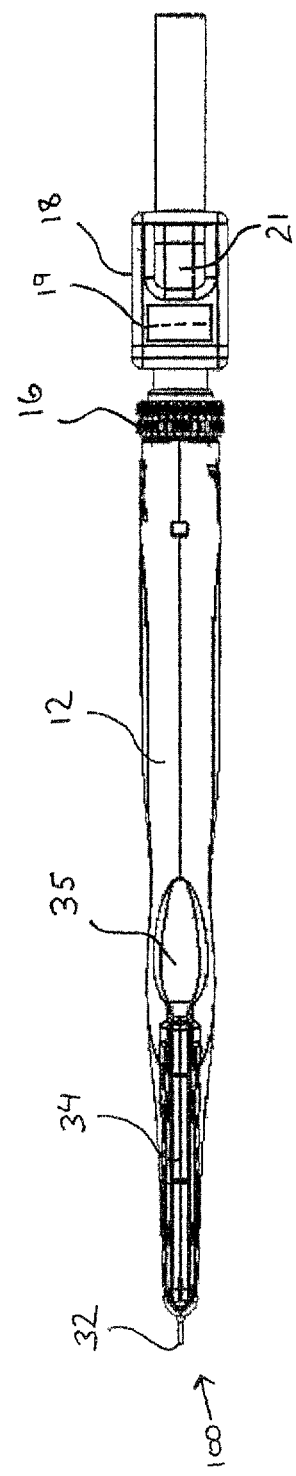
FIG. 7 is a top plan view of the embodiment in FIG. 1 illustrating the position of the finger rest, as well as other features.

In one embodiment, the body 12 of the probe 10 comprises a hollow interior cavity, for example, as shown in FIGS. 3 and 6. In a further embodiment, the hollow interior cavity 20 is essentially enclosed by the body 12, such that access to the interior is inhibited. But, in an alternative embodiment, the interior cavity 20 can be open or exposed along at least a portion of the probe bottom 400, permitting access to the interior cavity, as seen for example in FIG. 6.

The body 12 can comprise any of a variety of materials, such as, for example, plastics, rubbers, wood products, glass, metal, or various composites thereof, or any other material(s) having sufficient rigidity and durability. In one embodiment, the probe body comprises materials having limited flexibility, such that the body is generally rigid. This rigidity of the body helps to ensure that an accurate measurement is obtained when pressure is exerted on the probe tip. In a preferred embodiment, the body comprises one or more relatively inexpensive materials allowing disposability of the probe to be economically viable. In a further preferred embodiment, the body and/or components thereof comprise low weight materials, which can reduce fatigue and stress on the hand and arm of the user. For example, in one embodiment, the probe body 12 and certain components thereof, as discussed below, can comprise any of a variety of polypropylenes. In one embodiment, the probe body comprises a polypropylene having sufficient rigidity to reduce or prevent bending of the body, which can affect the accuracy of measurements. In a further embodiment, the sleeve 48 can comprise any of a variety of low-friction, thermoplastics, such as, for example, nylons or Acetals, which can reduce or prevent motion drag on the probe tip 32.

In a further embodiment, the shape of the body 12 encompasses ergonomic features that aid in the ease of use and comfort of the user. For example, in one embodiment, shown in FIG. 2A, the body shape comprises curvatures that can guide a dentist or hygienist in comfortably and correctly holding the probe. This can ensure that the probe is used properly for accurate measurements. This lends itself to a more compact probe body 12 design that requires less manufacturing material. Thus, in a further embodiment, the probe body 12 comprises a shorter, more compact design with ergonomic curvatures that aid in properly gripping the device. In a further alternative embodiment, the probe body can include various tactile indicators that can ensure that the hand and fingers are properly positioned on and/or around the probe body 12.

The interior cavity 20 can contain several of the movable working components of the probe 10. In one embodiment, the shape of the probe is conducive to positioning of the interior components. For example, in one embodiment, shown in FIG. 6, the curvature along the sides of the body translates into a narrower section 13 within the interior cavity 20. This narrow section 13 can aid in support and placement of a rod 30 that traverses the length of the body and a moveable arm 34 that translates movement of the probe tip 32 to the rod. It should be understood that the embodiment shown in the accompanying figures is for illustrative purposes and should not be construed as limiting.

It is well known that devices and equipment used with multiple patients must be cleaned and sterilized between each use. As discussed above, this can hinder progress in processing patients. Advantageously, the probe of the subject invention can be a single-use, disposable device, thus eliminating the need for between-patient cleaning of the device. In a further embodiment, to ensure that each probe is used only once or at least only on a single patient, the probe can comprise a break-away design that prevents it from being properly attached to the housing more than once.

In one embodiment, the body 12 is attached to the coupling 16 by positioning the proximal end of the body 12 around the coupling 16. In a preferred embodiment, the force required to position the body around the coupling is sufficient to achieve a secure and generally tight attachment prior to taking measurements, but still provides for relatively easy installation.

After treatment, the probe 10 must be removed from the coupling in order to attach a new, sterile probe to the coupling. In one embodiment, shown for example in FIGS. 10-13, the proximal end 200 of the body 12 that connects to the coupling 16 comprises a breakaway mount 11 that can be used to widen or break the proximal end of the body 12 for removal from the coupling. The breakaway mount 11 comprises a breakaway notch 15 and a breakaway tab 17. It can be seen in FIGS. 12 and 13 that the breakaway notch 15 extends between the interior cavity 20 to the proximal end 200 of the body 12. The position of the breakaway notch 15 forms a flange 22 between the interior cavity 20 and the proximal end 200 of the body 12, such that the flange 22 forms part of the proximal end of the body 12 that is affixed to the coupling 16, as seen, for example, in FIG. 11.

In one embodiment only the head or probe end of the probe breaks away and is disposable.

Figure 12:
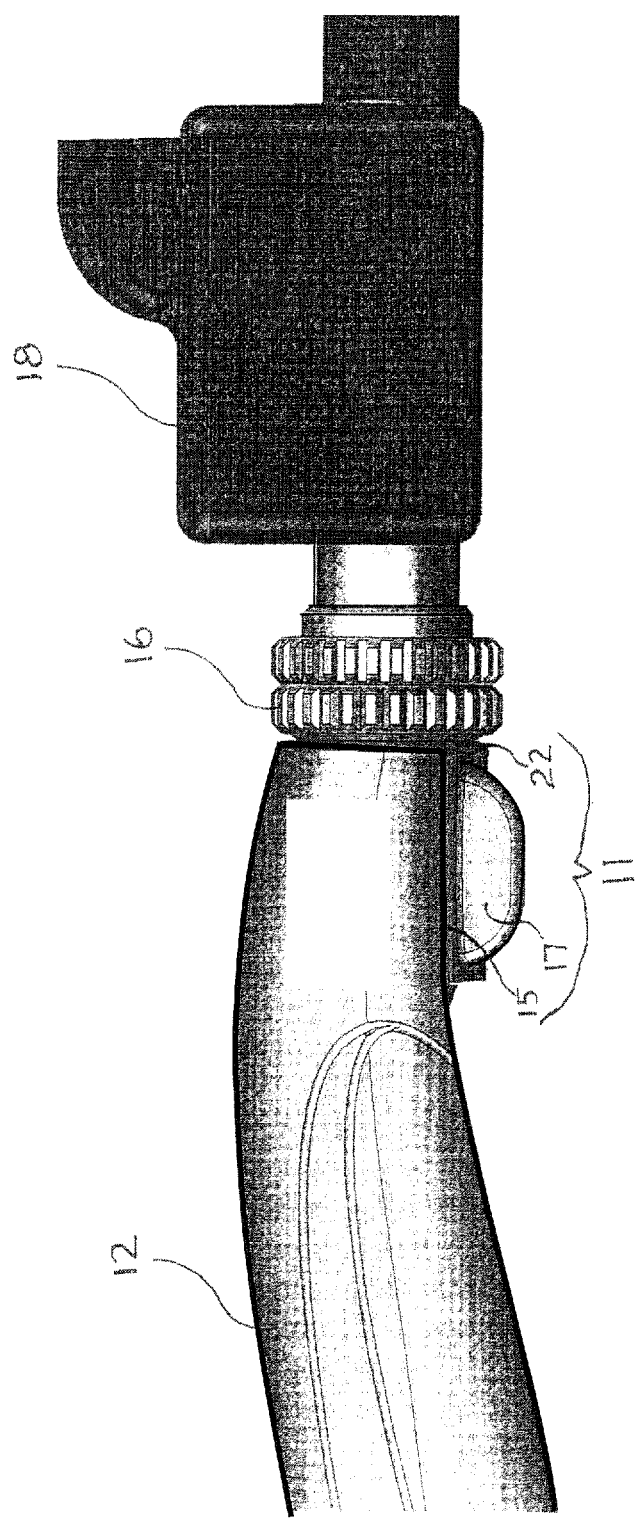
FIG. 12 is an enlarged left side plan view of the embodiment in FIG. 10 showing components of the breakaway mount.

In a further embodiment, the breakaway tab 17 is affixed to the flange 22. In a still further embodiment, the breakaway tab 17 is affixed to the flange in generally close proximity to the breakaway notch 15, for example, as shown in FIG. 12. In use, pressure exerted on the breakaway tab 17 causes the flange 22 to bend or, in an alternative embodiment, to break. Once the flange 22 is bent or broken away, the body of the probe 10 can be removed from the coupling without damage to the coupling or the housing. However, the probe cannot be reattached to the housing after the flange has been bent or broken. This ensures that the probe will be disposed of after use.

Figure 11:
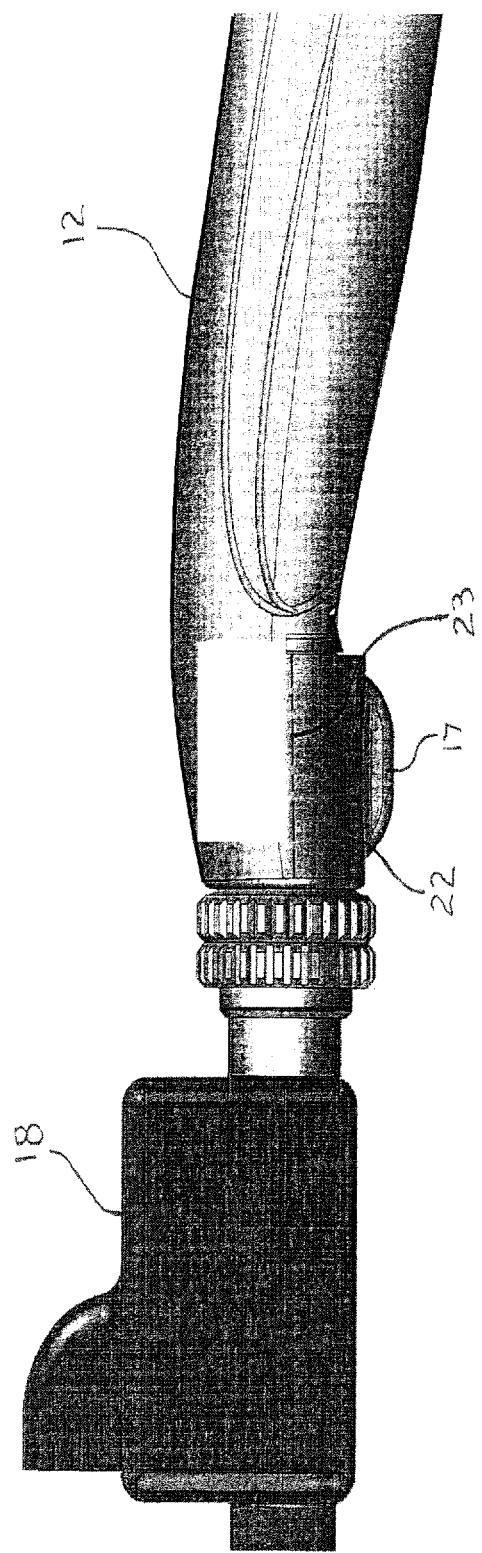
FIG. 11 is an enlarged right side plan view of the embodiment in FIG. 10 showing the components of the breakaway mount.
Figure 13:
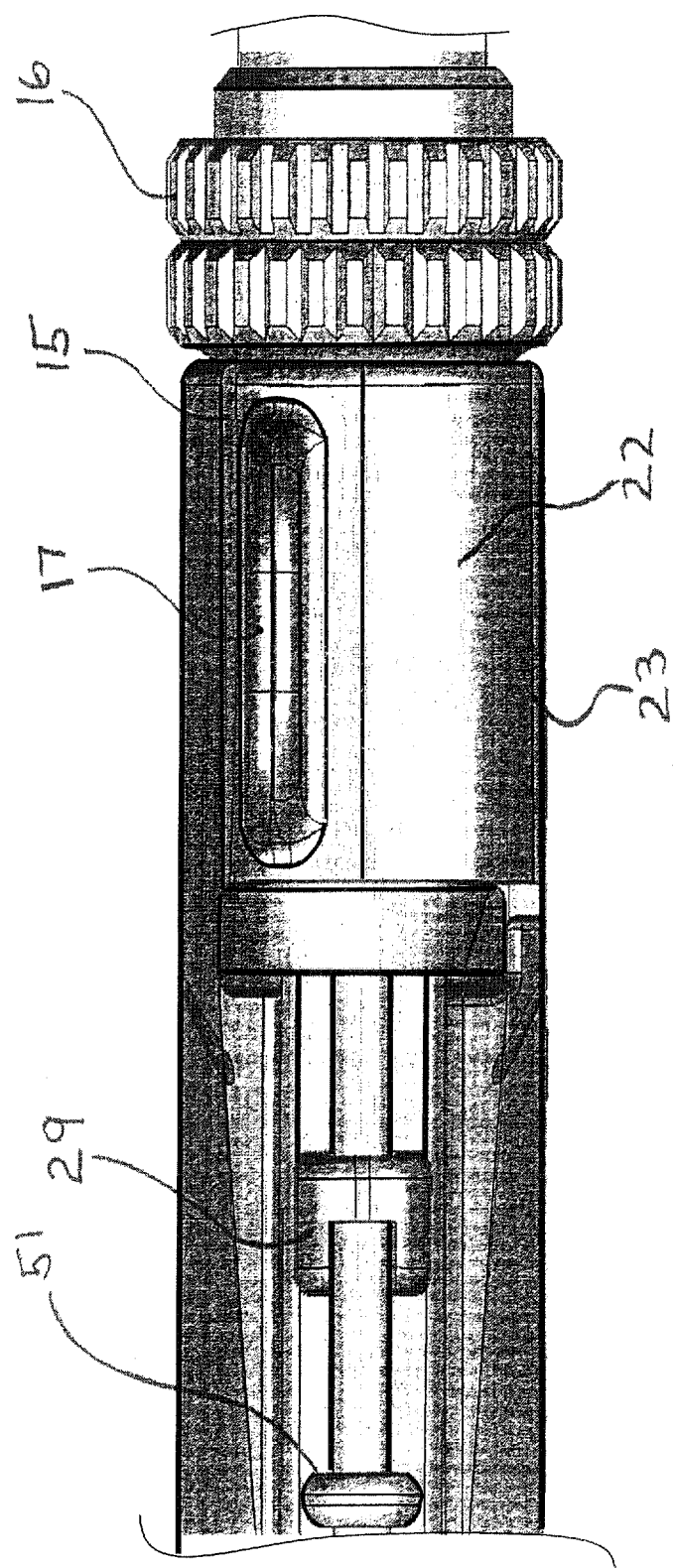
FIG. 13 is an enlarged bottom plan view of the embodiment in FIG. 10 showing the components of the breakaway mount.

In a further embodiment, the proximal end 200 of the body 12 comprises a break fault 23 at the point where the flange 22 attaches to the body 12, as shown, for example, in FIGS. 11 and 13. The break fault 23 is a specific area at which the flange 22 will bend or break when pressure is exerted on the breakaway tab 17, in the direction of the break fault 23. Break faults 23, or similar structures, are known in the art and it would be within the skill of a person trained in the art to recognize any of a variety of configurations that could be used with the subject invention.

Guiding a probe or any other device within the confines of an oral cavity requires significant skill and accuracy to avoid injury or pain to a patient. Naturally, visual acuity can be of utmost importance in most or all dental procedures. One embodiment of the subject invention includes a light within the body 12 of the probe that shines in the direction of the probe tip. In an alternative embodiment, the probe body 12 can comprise a translucent or semi-translucent material through which light can pass or be directed. In this embodiment, a LED (light-emitting diode) can be located in the housing 18 to which the probe 10 is attached. The LED light within the housing can be directed towards or guided by the material of the probe towards the distal end 100 of the probe and emitted therefrom to illuminate the interior of an oral cavity, and/or distal structures of the probe such as the probe sleeve 48, and/or the probe tip 32. A wide variety of techniques and apparatuses useful for guiding or directing light from an LED of the subject invention, e.g., fiber optic wire or cable and the like, will be apparent to those skilled in the art from the description provided herewith. Such alternatives are considered to be within the scope of the subject invention.

The interior cavity 20 contains the working components of the probe tip. The probe end 14, as seen, for example, in FIG. 3, has a tapered probe tip 32 pivotally attached to a movable arm 34. The probe tip can be pivotally attached by any of a variety of techniques known in the art. In one embodiment, the distal end of the movable arm 34 can have a slotted opening 38 into which the probe tip 32 is pivotally attached by a pin (not shown) placed through a bore traversing the slotted opening 38. In an alternative embodiment, a portion of the end of the probe tip that couples to the probe end 14 can be bent perpendicular to the probe tip forming a hook 37, similar to a clevis pin apparatus, for example, as shown in FIG. 4B. This embodiment eliminates the need for a separate pin and facilitates assembly of the probe, because the hook 37 on the probe end 14 acts as a pin and can be engaged with the bore 40 allowing the probe to pivot freely. In a further embodiment, a release slot 39, shown, for example, in FIGS. 3 and 4, can also be incorporated into the probe end 14 that can allow the probe 32 to be disengaged from the probe end 14. In this embodiment, the probe tip 32 can be rotated so that it is generally parallel with the release slot 39 allowing it to be slid through the release slot disengaging the hook 37 from the bore in the probe end 14.

In a further embodiment, probe tip 32 can have one or more graduation marks 44 located along at least a portion of the length of the probe tip. The graduation marks can be used as a visual indicator of the depth of the probe in a gingival sulcus. The graduation marks can be in any of a variety of configurations and/or scales known to those with skill in the art. In one embodiment, the graduations are delineated with marks. In a further embodiment, the marks are further indicated with an appropriate number, letter or color to clarify the depth of the probe. In a preferred embodiment, the graduation marks are in millimeters.

The probe tip 32 of the subject invention can be made from any of a variety of materials suitable for its intended use. For example, in one embodiment, the probe tip comprises the same materials used to manufacture the probe body and components thereof. Alternatively, the probe tip 32 comprises any of a variety of biocompatible materials suitable for taking measurements as described herein. For example, in one embodiment, the probe can comprise implant grade titanium. In this embodiment, the probe tip 32 can be slightly flexible, which provides better access to all areas of the teeth and gums of a patient. The space between the teeth and gums is relatively small and can be an extremely sensitive area in some patients. Thus, the diameter of the probe tip 32 can be important for the comfort of a patient. However, the probe tip should have sufficient strength to withstand the measurement process and, if necessary, additional force which can be applied to difficult areas. In an embodiment utilizing a titanium probe tip, the diameter can vary from approximately 0.40 mm to approximately 0.70 mm. In a still further embodiment of a titanium probe tip, the diameter can vary from approximately 0.45 mm to approximately 0.55 mm.

Figure 2:
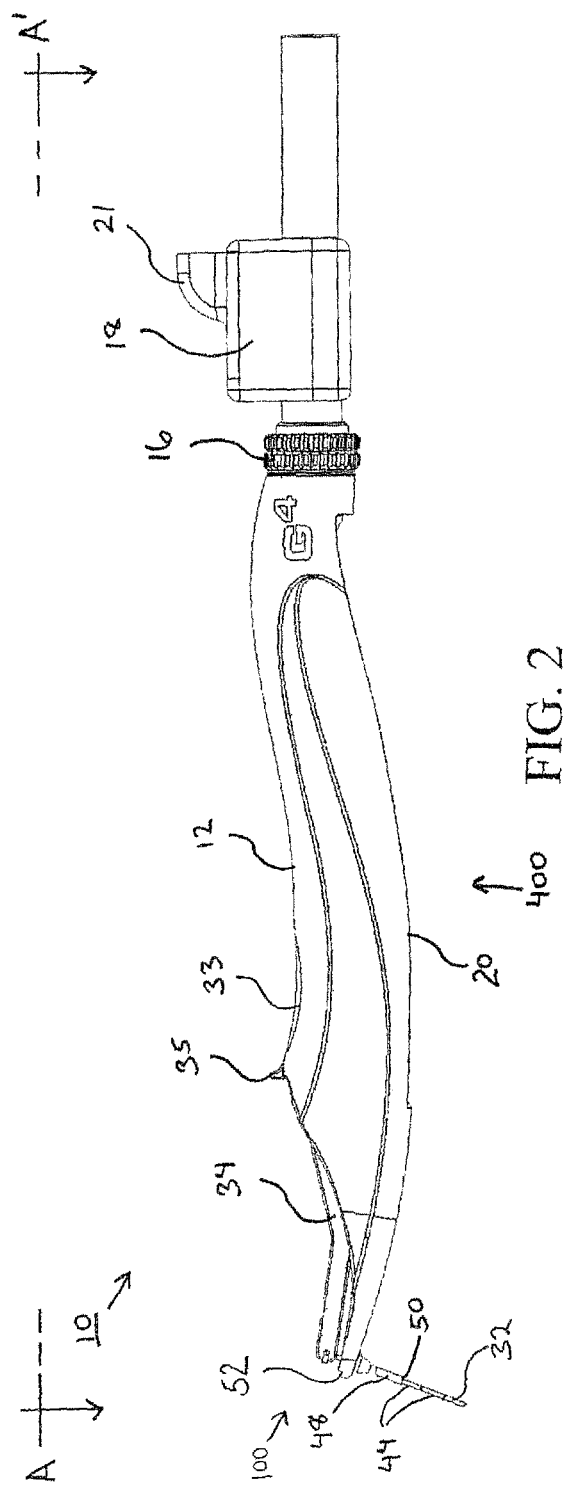
FIG. 2 is a side plan view of the embodiment of FIG. 1, illustrating the ergonomic details of the handle.

In a further embodiment, the probe tip 32 is positioned within and guided by a sleeve 48, as shown in, for example, FIGS. 2 and 4A. In one embodiment, sleeve 48 can be generally tubular having a consistent width along its length. But, in a more preferred embodiment, the sleeve 48 is tapered to a conical end 50, which can better control movement of the tip 32. In a further embodiment, the sleeve is located at the probe end 14, or distal end 100, of a fixed arm 52 that is integral to and extends from the bottom side 400 of the body 12, for example, as shown in FIG. 2.

In one embodiment, the sleeve 48 is fixedly attached, formed, or manufactured as part of, the probe end. In this embodiment, the sleeve is contiguous with, and inseparable from, the fixed arm 52. In an alternative embodiment, the sleeve can be a separate component capable of being fixedly attached to the fixed arm 52 at or near the probe distal end 100.

One embodiment utilizes a sleeve 48 that is permanently affixed to the bottom side 400 of the fixed arm 52, as illustrated, for example, in FIG. 4A. To affix the sleeve to the fixed arm, a variety of techniques can be employed, including, but not limited to, ultrasonic or other types of welding, crimping, heat sealing, or other methods and techniques known to those with skill in the art.

An alternative embodiment uses a sleeve 48 component that fits into position through the top side 300 of the fixed arm, at or near, the distal end 100. As mentioned above, the distal end 100 of the fixed arm 52 has a hole 53 that extends from the top side 300 to the bottom side 400 of the fixed arm that is at least partly contiguous with the central bore 57 of the sleeve.

Figure 4C:
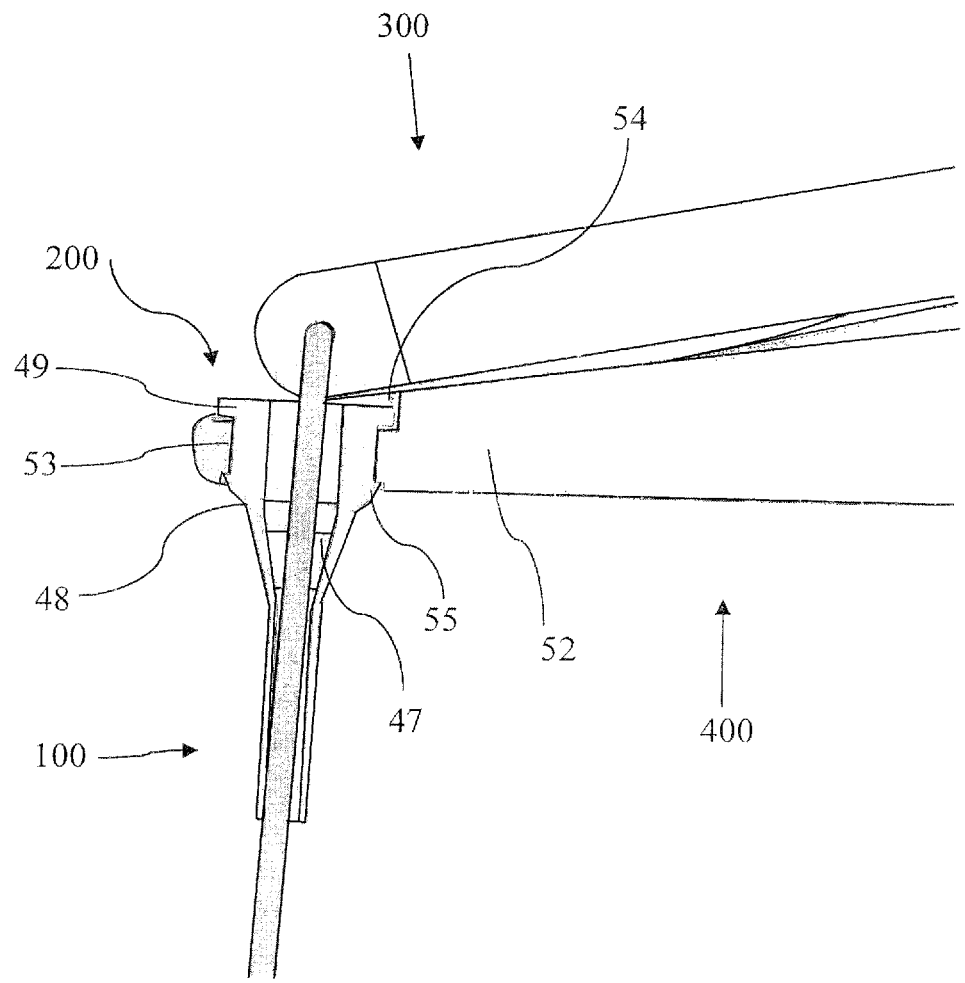
FIG. 4C is cross-sectional view of the probe distal end showing an alternative embodiment of the sleeve attachment.
Figure 5:
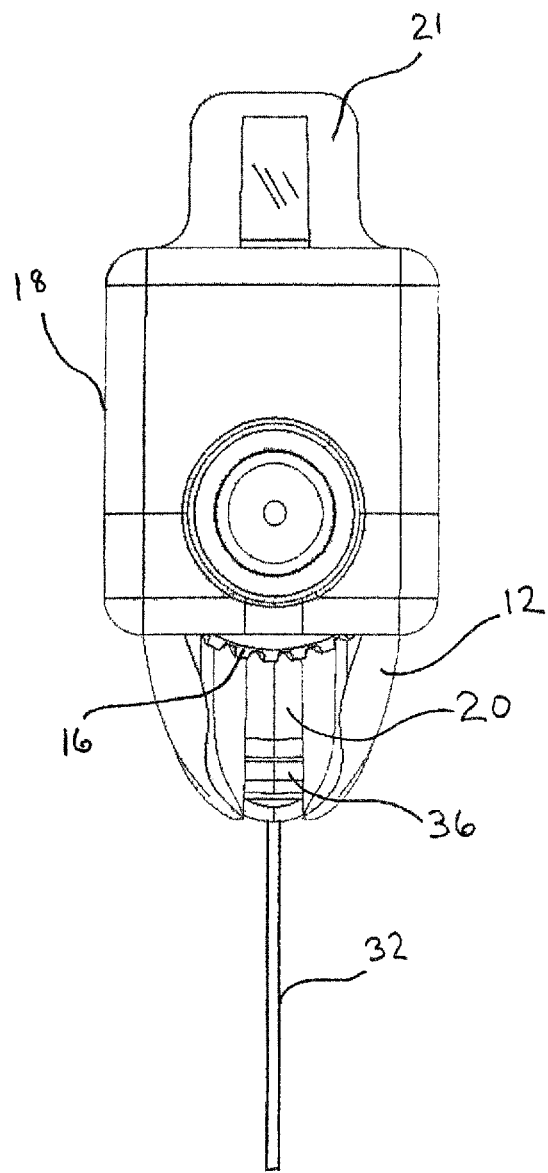
FIG. 5 is a rear plan view of the embodiment in FIG. 1, showing the wireless connection point on the displacement transducer.

In a further embodiment, a countersink 54 can be formed around the periphery of the top side 300 of the hole 53. In this embodiment, the distal end 100 of the sleeve 48 is maneuvered through the top side 300 of the hole 53 in the fixed arm until the proximal end 200 of the sleeve is cooperatively engaged with the countersink 54. In a further embodiment, the proximal end 200 of the sleeve 48 and the countersink 54 can have interdigitated profiles that facilitate their being cooperatively engaged. One embodiment, shown, for example, in FIG. 4C, has a locking ring 49 with a shape that is complementary to the countersink 54. In a further embodiment, the locking ring 49 and countersink 54 can have interdigitated profiles that facilitate their being snapped or pressed together, or otherwise fixedly connected. In an alternative embodiment, an example of which is also shown in FIG. 4C, the sleeve employs a pawl 55, surrounding all or some portion of the sleeve distal 100 to the locking ring 49. When the sleeve is passed through the hole, the pawl 55 can engage with the bottom side 400 of the hole 53, which prevents it from being retracted through the hole and separated from the fixed arm 52.

With the sleeve engaged through the top side 300 of the fixed arm, the probe tip 32 goes through the bore 57 in the sleeve 48, rather than the hole 53 in the fixed arm. Advantageously, in the unlikely event that the sleeve becomes disengaged from the fixed arm, this configuration makes certain that, it will not become separated from the probe, but will remain secured between the distal end of the probe and the probe tip.

Conical end 50 of the sleeve 48 further comprises a central bore 57, as shown for example (FIG. 4A) for guiding the tip 32. It can be seen in FIG. 3 that as force is applied to the end of tip 32 at the moveable arm 34 is forced towards the proximal end 200 allowing the tip to move upward in sleeve 48. In a further embodiment, the distal end 100 of the fixed arm 52 can have a hole 53 that extends from the top side 300 to the bottom side 400 of the fixed arm and that is at least partly contiguous with the central bore 57 of the sleeve, for example, as shown in FIG. 4A. In this embodiment the probe tip 32 goes through the hole 53 in the fixed arm, as well as through the bore 57 in the sleeve 48.

The sleeve can be made from any of a variety of materials known to those with skill in the art. For example, the sleeve can comprise the same or similar materials as the body and/or components thereof. Alternatively, the sleeve can comprise any one of a number of biocompatible materials. Preferably, the sleeve material should provide sufficient rigidity to accurately guide and control the probe tip. But, it should also have slight, but sufficient, flexibility to prevent binding or interference of movement of the probe tip within and through the sleeve.

In a further embodiment, the sleeve material can comprise a generally bright color to aid in the measurement process. The probe of the subject invention measures the depth of a gingival sulcus as the distance from the tip of the probe, positioned at the bottom of the pocket, to the height of the gum tissue, measured at the conical end of the sleeve 50. Thus, it can be helpful if the sleeve is a bright color that is easily seen within the oral cavity.

During the measuring procedure, blood and other viscous fluids from the gum tissues can often be transferred from the probe tip 32 into the sleeve 48. This can cause a viscous drag on the probe tip. Addition of a lubricant, such as glycerin, through the lumen of the probe tip would reduce this viscous drag.

Further, reaching all of the points required for a thorough exam can be difficult, particularly when trying to reach teeth in the back of the mouth or through oral appliances, such as braces or bridgework. Thus, in a further embodiment, the probe tip 32 of the subject invention is slightly flexible, allowing it to bend for better reach in-between teeth and other difficult oral areas. In addition, the flexible sleeve can reduce friction on the probe tip allowing for more accurate readings and less probing force.

The combined probe tip with the sleeve can lend considerable access to all of the teeth and gums of a patient. The probe of the subject invention can ensure that accurate measurements are taken in all areas of the teeth and gums to help in diagnosing and monitoring the presence and progression of periodontal disease. However, once presence of the disease has been positively determined, prevention of further gum, or tooth degradation is often the primary concern of a dental professional and the patient.

The application of various medicaments to the teeth and gums can aid in treatment of periodontal disease and or the pain associated with the disease or dental procedures, including measurement of pockets. Thus, in one embodiment, the probe tip of the subject application is hollow. And, in a further embodiment, the proximal end of the hollow probe tip can be connected to a tube or hose that supplies a medicament. The application of oral medicaments utilizing the probe tip of the subject invention can permit direct, localized application of any of a variety of medicaments used in dentistry, including, but not limited to, mouthwash, painkiller, antibiotics, dye, cleansers, and other orally applicable products. The medicament may be a solid, liquid, or gas, including gels and suspensions.

Thus, the subject invention provides a probe tip capable of measuring a gingival sulcus to diagnose and monitor the presence of periodontal disease, as well as for applying one or more medicaments for the treatment of, or relief from, the disease or for other oral procedures. Such application of medicaments can be done in conjunction with obtaining measurements. For example, they can be done contemporaneously, such as within 5 seconds, or preferably 2 seconds of each other, or simultaneously.

The movable upper arm 34 is supported and held in place within the body 12 by a strut 36 at the bottom end 100 of the movable upper arm 34, as seen in FIG. 3, around which it can rotate. Thus, as the movable upper arm pivots around the strut 36, it rotates against a rod 30 that is under constant force of a spring 28. In one embodiment, the movable arm comprises a notch 31 that can be snapped into place against the strut 36, rotatably attaching the movable arm to the strut.

The rod 30 is pivotally connected or otherwise in contact at its distal end 100 to the movable arm 34 at notch 62. The proximal end 200 of rod 30 is in operable connection or otherwise in contact with a displacement transducer 64 located within the housing 18, which generates electrical signals corresponding to the movement of the probe tip 32. In one embodiment, the displacement transducer 64 is in operable connection to a digital readout 19 located on the exterior of the housing 18. In an alternative embodiment, shown, for example in FIG. 9, the digital readout 19 can be a separate unit. In an alternative embodiment, the displacement transducer 64 is in operable connection to any of a variety of radio frequency (RF) transmitters 21, known in the art, which can transmit data to a computer 66.

Thus, the motion of the probe tip is translated through the movable arm 34 and the rod 30 to the displacement transducer. In one embodiment, the configuration of the probe tip, moveable arm and rod causes motion translation of a 1:1 ratio. However, the range of motion of the probe tip 32 can be as much as 5 to 6 millimeters, which at a 1:1 ratio can necessitate a relatively large displacement transducer. Thus, in an alternative embodiment, the configuration of the probe tip, moveable arm and rod provides a 3:1 reduction in motion translation between the probe tip and the displacement transducer. This facilitates accurate measurements by a smaller displacement transducer. A reduction in motion translation can also reduce the effect of minor movements unrelated to the measurement process.

As mentioned above, the probe body 12 can provide support to the interior components of the probe 10. Thus, in one embodiment, the rod 30 is supported by at least a portion of the walls of the interior cavity 20, as shown, for example, in FIG. 6. In a further embodiment, the interior cavity 20 further comprises a bracket 29 at or near the proximal end 200 of the probe body that supports the proximal end of the rod, for example, as shown in FIG. 3.

Multiple types of displacement transducers are commercially available and can be used for converting the mechanical displacement of rod 30 into one or more electrical signals that can be transmitted to a computer 66. A linear variable differential transformer (LVDT), a potentiometer, and an optical encoder are three common types of displacement transducers that could be used with the invention. However, a person skilled the art would be able to determine other types of displacement transducers that could be utilized with the subject invention. In one embodiment, a housing 18 can be utilized to support the displacement transducer 64. Further, a person with skill in the art would be able to utilize any of a variety of apparatuses that can be used to operably connect the displacement transducer 64 to coupling 16 at the end of the probe body 12, such that it is in operable connection to rod 30.

Figure 9:
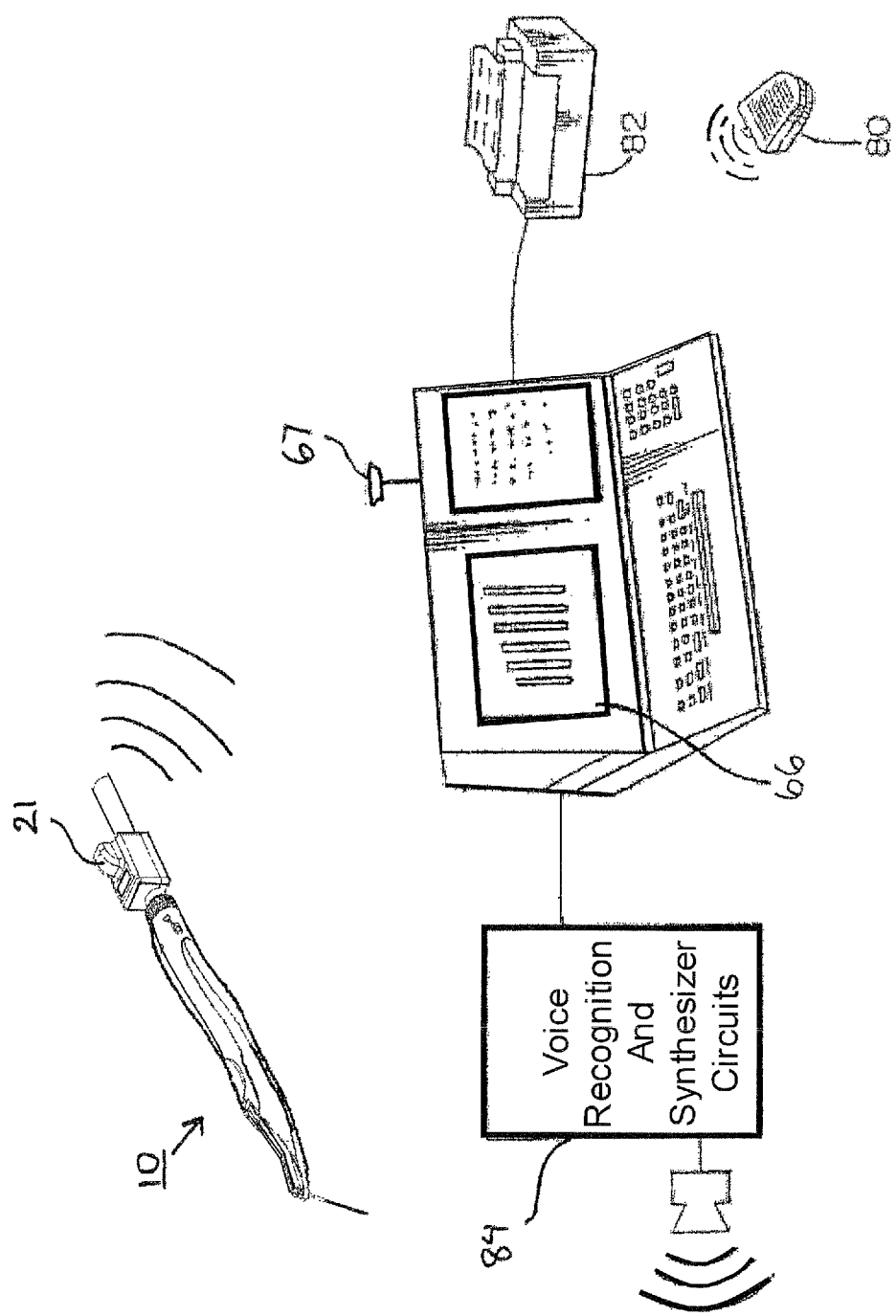
FIG. 9 illustrates an embodiment of the periodontal probe with a wireless connection to a computer. In this embodiment, a foot pedal is employed to trigger the transmission of a measurement to the computer, once the probe is properly positioned. A printer can also be operably connected to the computer for printing measurement data.
Figure 10:
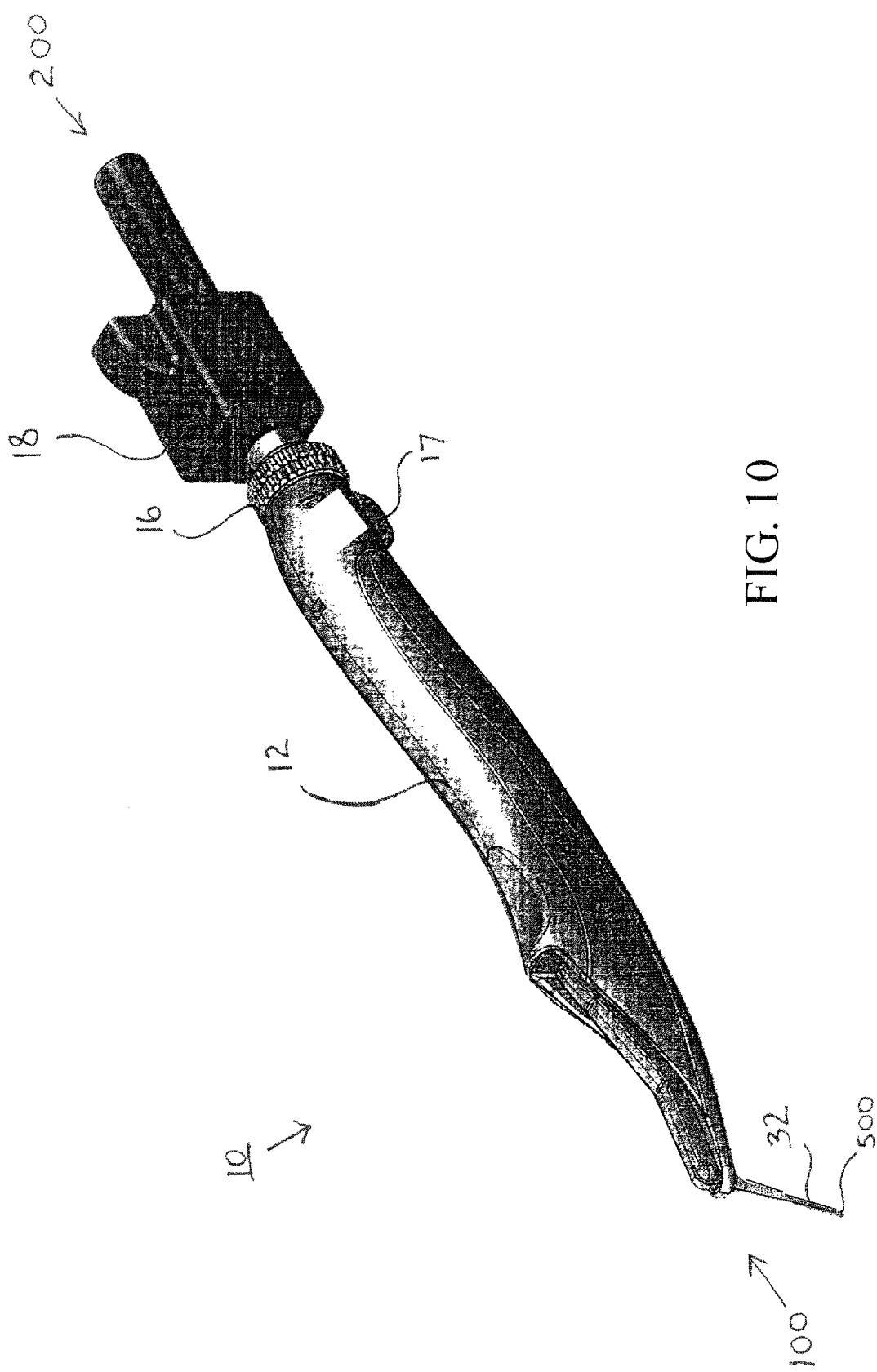
FIG. 10 is an isometric view of an embodiment that utilizes a break-away mount between the probe and the housing.

In operation, the movement of rod 30, which correlates to the position of the movable arm 34 and the probe tip 32, activates the displacement transducer. The output of the displacement transducer can be translated to the RF transmitter 21, which is capable of wireless transmission of signals and information to a computer interface receiver 67. In a further embodiment, a foot switch 80 can also be connected to the computer interface 66 that when pressed causes the electrical signal from the displacement transducer to be transmitted to and recorded by a computer 66. In a further embodiment, a representative example of which is shown in FIG. 9, the action of the foot switch 80 can also be made wireless.

In a further embodiment, the foot switch can comprise one or more foot operated buttons that can be used to control the information sent to a computer interface. For example, in one embodiment, mentioned above, a switch can be used to transmit the readings, i.e., measurements, obtained by the displacement transducer. In a further embodiment, the foot switch can comprise a button or switch that can recall or delete one or more previous entries, or indicate that an area or site is being skipped or taken out of order, as well as other signals. A person with skill in the art would be able to devise any of a variety of devices and/or techniques that could be utilized to input information to a computer from a foot pedal device and such modifications are considered to be within the scope of the present invention.

Any of a variety of displacement transducers known in the art can be employed with the probe 10 of the subject invention. For example, one type of displacement transducer that can be used with the present periodontal probe 10 is an optical encoder. The transducer positioned in the housing can be placed in contact with the proximal end 200 of rod 30. A person with skill in the art would readily recognize any of a variety of displacement transducers that can be used to measure the movements of rod 30, and such variations are contemplated to be within the scope of the subject invention. Further, it would be well within the skill of a person trained in the art to utilize known devices to contrive any of a variety of methods and devices for interfacing a displacement transducer with an RF transmitter for interfacing with a computer, and such variations are considered to be within the scope of the subject invention.

Alternative embodiments could utilize other types of triggering sensors, such as, for example, verbal command or other sound sensors, motion detector sensors, or other devices to trigger the displacement transducer 64 to transmit a signal, or otherwise cause a probe measurement or other information to be recorded by a computer 66. In one embodiment, the sensor can be activated by a sound or motion from a dentist that does not require using the hand or arm manipulating the probe, or the dentist removing their eyes from the patient. It would be well within the skill of a person trained in the art to create any of a number of devices that could be utilized to trigger or signal the recording of a probe measurement on a computer. Such variations are considered to be within the scope of the present invention.

From the above description and the accompanying figures, the interconnection can be seen of the components of the probe of the subject invention. With reference to the accompanying figures, which show one possible embodiment, the probe can be seen to comprise a probe tip 32, positioned within a sleeve 48 on a fixed arm 52, having operable contact with a moveable arm 34, being supported on the bottom side 400, by a strut 36, and a rod 30 having operable contact at one end to the top end 300 of the movable arm and at the proximal end to a spring 28. In this embodiment, it is the combination of the spring tension and the positioning of the probe tip within the sleeve that act to maintain the position of the various components and allow the probe tip to operate as described above. By hyper-extending the probe tip towards the top of the probe 300, the rod 30 can be bent sufficiently that the probe tip 32 can be disengaged from the sleeve, which can allow the probe to be disassembled, such that the rod and movable arm can be disengaged and removed, if desired from the body of the probe. In a further embodiment, a stop 51 can be fixedly affixed to, or comprise part of, the rod, an example of which is shown in FIGS. 3 and 13. The stop 51 can be placed a sufficient distance from the bracket 29 to allow movement of the rod as required for obtaining measurements. However, the stop 51 can prevent over extension of the rod into the housing and damage to the internal housing components.

This allows for the component parts to be manufactured separately and assembled prior to use, either at the point of manufacture, or later.

The sensitivity of the probe of the subject invention can be adversely affected during transport and storage without proper protection. Thus, it can be helpful if the probe or at least the distal end thereof, is covered or otherwise surrounded with a protective sheath or material. In one embodiment, a protector cover can be utilized to protect the probe end 14, including the probe tip 32, prior to use. In this embodiment, the protector cover can be removed from the periodontal probe to expose the probe end. However, in an alternative embodiment, the probe 10 can be packaged in such a way that the probe is protected for transport and storage purposes. Thus, in one embodiment, a probe of the subject invention can be packaged into any of a variety of protective packaging products known to those with skill in the art. For example, blister packs, clamshell containers, and thermoformed trays can all be used to package the probe of the subject invention.

In a preferred embodiment, the probe is secured within the packaging such that the distal end 100 where the probe tip 32 is located cannot come into contact with the walls of the packaging. Properly securing the probe within the package can reduce or prevent opportunity for the probe tip or sleeve to be damaged, bent or otherwise rendered unusable during transport or storage. In one embodiment, the probe can be packaged individually. But, in a further embodiment, a plurality of probes could be packaged and secured in a single container. A single sealed container can contain several probes, and be sealed such that it can be partially opening the packaging will expose one probe at a time. Such secure packaging products and techniques are known to those with skill in the art. As such, modifications will be apparent to such skilled artisans having benefit of the current disclosure and are contemplated to be within the scope of the present invention.

Figure 8:
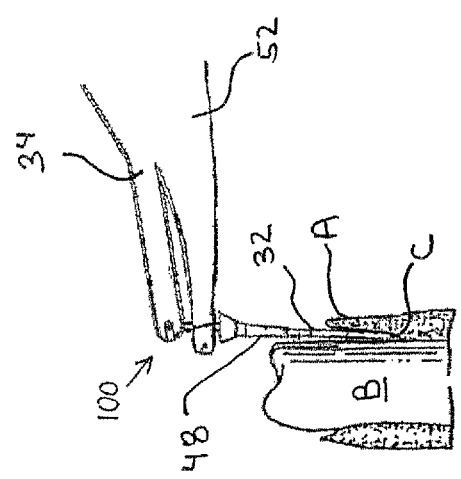
FIG. 8 illustrates how the probe device of the subject invention is utilized in measuring a gingival sulcus.

The proximal end 200 of the probe 10 is connected to the coupling 16 at the distal end 100 of the housing, such that the rod is in operable connection with the connector 16 to which the displacement transducer also has an operable connection. The probe tip 32 can be placed at the bottom of the periodontal pocket C, as shown, for example, in FIG. 8, located between tooth B and gum A. Once the probe tip 32 is correctly positioned within the pocket, sleeve 48 is pushed towards the pocket, causing the rod 30 to be moved proximally 200 against the tension of the spring 28. When the bottom end of the sleeve 48, or the conical end 50, contacts the margin of the gum A a measure can be taken that represents the depth of the pocket. In one embodiment, the pocket depth can be visually observable on a digital readout 19. But, in an alternative embodiment, the pocket depth can be permanently recorded on a computer 66 or other recording apparatus when a foot pedal 80 is pushed.

In a further alternative embodiment, audio sounds from the computer, such as, for example, via a tone generator or a voice synthesizer 84 can also be utilized with a computer. This would allow audio feedback from a computer that can, for example, assist a dentist in probing in the correct sequence, indicate an error in a measurement, or other information. In a further embodiment, a computer could be utilized to receive verbal information, such as with voice recognition software, as known in the art. This would allow a hygienist to record measurements, or even other information, by verbalizing the information and measurements. For example, voice recognition software can be utilized to recognize specific words, e.g., "blood", "fluid", "recession", etc. A person with skill in the art would be able to determine any of a variety of devices, methods and software known in the art for voice synthesizer and/or recognition electronics that can be used with computers for these purposes and such variations are contemplated to be within the scope of the subject invention.

In a further embodiment, the configuration and design of the probe can incorporate a variety of ergonomic features that improve measurement accuracy and comfort for a dentist or hygienist. In one embodiment, the probe body 12 can include a finger pad 33 and a finger rest 35, examples of which are shown in FIGS. 1, 2A, and 4A. In use, the probe 10 is usually held between the index finger and thumb. In one embodiment, the finger pad 33 can be a flattened or semi-flattened area on the top side 300 of the probe body 12. In a further embodiment, the finger pad 33 can comprise any of a variety of peripheral shapes and can further include raised dimples or ridges or similar protrusions, or depressions or recesses to aid in gripping the probe. The location of the finger pad 33 is preferably at or near the top of the probe 300. But, in a more preferred embodiment, the finger pad is located at generally the center of the top of the probe 300, as shown, for example, in FIG. 1. And, in a still further preferred embodiment, the finger pad is positioned at or near the distal end 100 of the probe body 12.

During the positioning of the probe tip 32 within a pocket, it can be necessary to immobilize the moveable arm temporarily in order to move the probe tip 32 past the gum line. For the subject invention this can be achieved by pressing on the top side 300 of the movable arm 34 to prevent the probe tip 32 from sliding into the sleeve 48 while navigating the probe tip past the gum line. Once the probe tip 32 is moved past the gum line and inserted within a pocket, the movable arm can be released so that a measurement of the pocket can be taken. Because of the sensitivity of the spring 28, which provides the constant pressure to the probe tip, it is important that the movable arm 34 not be hindered in any way. Otherwise, it may not be possible to obtain an accurate measurement(s) because the reading(s) transmitted to the displacement transducer 64 will be adversely affected by the accidental pressure on the movable arm 34.

To prevent accidental contact with the movable arm 34, the probe of the subject invention can further comprise a finger rest 35 fixedly attached to the probe body 12. The finger rest 35 provides a convenient and comfortable pressure point against which the index finger can exert pressure when inserting the probe tip 32 into a pocket. But, it can also reduce or prevent accidental contact with the movable arm 34. FIGS. 1 and 2A show an embodiment wherein the finger rest 35 is a protruding flange positioned at or near the distal edge 100 of the top side 300 of the probe body 12. The finger rest 35 can be any suitably tall protrusion or extension on the probe body 12 to prevent accidental contact with the movable arm 34. In one embodiment, the finger rest 35 extends generally vertically from the probe body and is sufficiently tall enough for the index finger to rest against or on for stability when holding the probe, but easily traversed when direct contact with the movable arm is desired to secure the probe tip.

In an alternative embodiment, the finger rest 35 can comprise a less prominent protrusion to prevent or reduce accidental contact with the inside of a mouth during a procedure. Thus, in one embodiment, the finger rest 35 comprises at least one raised dimple, ridge or similar tactile protrusion that can provide a physical reminder to a dentist or hygienist that the position of their finger is moving past a safe point on the finger pad 33 and may be inhibiting the movable arm 34.

In a complete examination, at least six points are probed on each tooth. Therefore, a patient having all thirty-two teeth can require a total of 192 pocket depth recordings. In one embodiment, software for use on a computer can be utilized to determine the probing order for each pocket so that the data are labeled properly and consistently between patients. Such software can account for missing teeth as well to ensure proper labeling of each measurement. In a further embodiment, the computer and related software can provide a visual picture that can remind the dentist which point should be probed next. In still further embodiments the computer can be programmed to back up and/or to move ahead in the sequence so that corrections can be made. In a yet further embodiment, a continuous plot of the pocket depth can also be obtained by sliding the probe tip at a uniform rate along the floor of the pocket while the depth is recorded on a time base plot. A person with skill in the art would be able to determine any of a variety of measurement data that can be obtained with a probe of the subject invention and such variations are considered to be within the scope of the subject invention.

The pocket depth data obtained by a computer can be stored on any of a variety of computer readable media known in the art, including, for example, hard drive disks, floppy disks, flash drives, CD, DVD, or other optical media. In a further embodiment, a hard copy for the patient's file (chart) can be printed if desired. Preferably, the data are stored on a medium that can be available for recall to compare with later probings, so as to monitor a patient's changes in status over many years.

The diagnosis of periodontal disease is an important procedure because the avoidance of periodontal disease can be vital for the overall health and comfort of a patient. Unfortunately, the diagnosis of periodontal disease with periodontal probing can be painful for patients. The pain caused by probing can discourage or delay patients from seeking to have the procedure done and/or delay having treatment if a need for treatment is identified. Therefore, methods to reduce pain associated with probing are very helpful. Also, the ability to provide treatment at the time of diagnosis can be a significant advantage in prevention and/or control of periodontal disease.

In one embodiment the probe of the subject invention is adapted for the dual role of diagnosis and therapy. In one embodiment, the probe 10 has one or more containers that store one or more treatment materials. Such treatment materials can be, for example, antibiotics, chemotherapeutics, anesthesia, dyes, probiotic therapies, mouthwashes, fluoride, anti-sensitivity products, and any of a variety of rinses.

In one embodiment, the material in the container can be under pressure so that when activated by a dentist or hygienist, the treatment material is released. In a further embodiment, a container can pressurized and calibrated to eject a specified amount of treatment material.

Any of a variety of containers can be used with the probe of the subject invention to administer treatment materials or medicaments. By way of a non-limiting example, one or more pressurized bags, cylinders, or ampoules of appropriate size can be within the interior cavity, or affixed to the exterior body, of the probe. A person with skill in the art and benefit of the subject disclosure would be able to determine appropriate container(s) and pressure(s) required to administer treatment material(s)

In a further embodiment, the probe tip 32 of the subject invention can be connected to the container and utilized to administer treatment(s) below the gum line. In one embodiment, the probe tip 32 of the subject invention can be hollow and administer treatment through the probe tip distal end 500. In an alternative embodiment, a modified probe tip can be utilized with the subject invention, wherein the probe is hollow, but formed with a round-blunted end. A round-blunted end can aid in moving the probe tip past the gum line and reduce pain to a patient. The opening in the probe tip distal end can be formed at the terminal end of probe tip distal end 500. Alternatively, the opening can be formed into the side of the probe tip in the general proximity of the probe tip distal end so that the end can be fully rounded, but treatment material can still be applied below the gum line. In a still further embodiment, there can be more than one opening at or near the probe tip distal end 500.

Dental examinations are often avoided by patients, especially those with periodontal disease. It can be beneficial to obtain measurements and administer medicaments during the same appointment. Thus, the application of medicaments can be done at any point before, during, or after an examination. For example, in one embodiment, the application of medicaments is done in conjuction with obtaining measurements. In a further embodiment, the application of medicaments is done contemporaneously with taking measurements, that is within approximately 5 seconds, preferably 2 seconds, of obtaining a measurement. In a still further embodiment, the application of medicaments is done simultaneously with taking a measurement.

As discussed above, the probe 10 of the subject invention can be operatively connected to a computer that can automatically, or on command, record measurements. In a further embodiment, the system can include a treatment regimen administered at the time measurements are taken. This provides the advantage of being able to diagnose and treat a diseased area with a single probe event. It can also reduce or prevent the distribution of the organisms of disease throughout the mouth, since the probe tip will be exposed to the medicament prior to moving to another site.

In one embodiment, the computer can be programmed to emit a signal whenever it receives a particular measurement obtained by the displacement transducer from a patient. This allows the hygienist or dentist to administer a treatment medicament before the probe is moved or displaced from below the gum line. Alternatively, the hygienist or dentist can administer a treatment medicament upon receiving a signal from the computer.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

It should be understood that, although the present invention has been described with reference to specific details of certain embodiments thereof, it is not intended that such details should be regarded as limitations upon the scope of the invention except as and to the extent that they are included in the accompanying claims.

We claim:

1. A periodontal pocket depth probe comprising:
    an elongate body having a distal end, a proximal end, and a hollow interior cavity traversing the length of the elongate body;
    a fixed arm located at the distal end of the elongate body;
    a movable arm having a distal end and a proximal end, wherein the proximal end is movably attached at the distal end of the hollow interior cavity of the elongate body and is further operably attached to a displacement transducer;
    one or more containers affixed to the elongate body, where at least one of the containers is configured to apply a substance in at least one pre-determined amount; and
    a hollow probe tip, at the distal end of the moveable arm, where the hollow probe tip is operably connected to the one or more containers and has at least one opening at or near the probe tip distal end,
    wherein the hollow probe tip is adapted to transmit probing depth data to a displacement transducer through the moveable arm, such that transmission of at least one pre-determined subgingival pocket depth causes the at least one pre-determined amount of the substance in the container to be applied subgingivially and while contemporaneously performing at least one of obtaining probing depth data and transmitting probing depth data to a displacement transducer.

2. The periodontal depth probe, according to claim 1, further comprising:
    an elongated tubular sleeve having a central bore therethrough, a tapered distal end and that extends from the distal end of the fixed arm;
    the moveable arm having the proximal end pivotally attached at the distal end of the hollow interior cavity of the elongate body; and
    a rod having a distal end, in operable connection to the proximal end of the movable arm, and a proximal end, in operable connection with a spring that biases the rod towards the distal end of the elongate body and further operably connects the rod to the displacement transducer;
    a pivotal connection between the hollow probe tip and the distal end of the movable arm, so that the hollow probe tip extends through and reciprocates within the tubular sleeve central bore, thereby transmitting probing depth data to the displacement transducer through the moveable arm and the operably connected rod.

3. The periodontal depth probe, according to claim 1, wherein the at least one opening in the hollow probe tip is located on a side of the probe tip in proximity to the distal end.

4. The periodontal depth probe, according to claim 1, wherein at least one of the one or more containers is affixed to the exterior of the elongate body.

5. The periodontal depth probe, according to claim 1, wherein at least one of the one or more containers is affixed within the hollow interior cavity of the elongate body.

6. The periodontal depth probe, according to claim 1, further comprising a light for illuminating the probe tip.

7. The periodontal depth probe, according to claim 1, further comprising
    a radio frequency transmitter in operable connection with the displacement transducer;
    a computer in operable connection with the radio frequency transmitter; and
    a switch in operable connection to the computer
    such that probing depth data from the hollow probe tip is translated through the moveable arm to the displacement transducer, which transmits the probing depth data to the radio frequency transmitter, where it is further transmitted to the computer, whereby activation of the switch signals the computer to record the information being transmitted at that time to the computer.

8. The periodontal depth probe, according to claim 7, wherein the computer emits a sound to indicate that substance should be applied.

9. The periodontal depth probe, according to claim 7, wherein the switch is activated by sound.

10. The periodontal depth probe, according to claim 7, wherein the switch is voice activated.

11. The periodontal depth probe, according to claim 1, wherein the container is pressurized.

12. A method for measuring dental pocket depth utilizing a periodontal depth probe of claim 7, said method comprising:
    (a) affixing the probe to the displacement transducer;
    (b) placing the distal end of the hollow probe tip below a gum line and into a dental pocket;
    (c) exerting sufficient force on the probe tip with the probe elongate body to cause the tapered distal end of the sleeve to move closer to or in contact with the gum line;
    (d) activating the switch to signal the computer to record the distance between the distal end of the probe tip and the gum line indicated at that time by the displacement transducer;
    (e) maintaining the probe tip below the gum line until the computer determines if the at least one pre-determined amount of substance should be applied and provides an indication of such;
    (f) applying the at least one pre-determined amount of substance if indicated to do so;
    (g) repeating steps (a) through (f) as necessary;
    (h) removing the probe from the displacement transducer.

13. The method, according to claim 12, wherein the measurements are recorded by a computer in operable connection to the probe.

14. A method for simultaneously delivering a substance to or within the gums of a patient and measuring dental pocket depth utilizing a periodontal depth probe of claim 2, said method comprising:
    (a) affixing the probe to the displacement transducer;
    (b) connecting the hollow probe tip, with at least one opening at or about the distal end, to one of the one or more containers affixed to the elongate body of the probe and containing the substance to be delivered;
    (c) placing the at least one opening in the distal end of the hollow probe tip below the gum line and into a dental pocket;
    (d) exerting sufficient force on the hollow probe tip with the elongate body to cause the tapered distal end of the sleeve to move closer to or in contact with the gum line;
    (e) recording the distance between distal end of the probe tip and the gum line indicated by the displacement transducer;
    (f) determining whether a pre-determined amount of the substance should be applied to the dental pocket based on the recorded distance;
    (g) applying the pre-determined amount of the substance from the at least one probe tip opening, if determined to be required in step (f);
    (h) repeating steps (a) through (f); and
    (i) removing the probe from the displacement transducer.

15. The method, according to claim 14, wherein the substance is a medicament.

16. The method according to claim 15, wherein the medicament comprises a lubricant.

\* \* \* \* \*